US006281202B1

(12) United States Patent
Magnani et al.

(10) Patent No.: US 6,281,202 B1
(45) Date of Patent: Aug. 28, 2001

(54) PHARMACEUTICAL COMPOSITIONS FOR TREATMENT OF EGF RECEPTOR ASSOCIATED CANCERS

(75) Inventors: John L. Magnani, Rockville, MD (US); Eric G. Bremer, Western Springs, IL (US)

(73) Assignee: GlycoTech Corp., Rockville, MD (US)

(*) Notice: Subject to any disclaimer, the term of this patent is extended or adjusted under 35 U.S.C. 154(b) by 0 days.

(21) Appl. No.: 09/379,016

(22) Filed: Aug. 23, 1999

Related U.S. Application Data

(62) Division of application No. 08/679,643, filed on Jul. 12, 1996, now Pat. No. 6,008,203.
(60) Provisional application No. 60/001,150, filed on Jul. 15, 1995.

(51) Int. Cl.$^7$ .................................................. A61K 31/715

(52) U.S. Cl. ............................................. 514/61; 536/53

(58) Field of Search ................................. 514/61; 536/53

(56) References Cited

U.S. PATENT DOCUMENTS

| | | | |
|---|---|---|---|
| 3,336,155 | 8/1967 | Rowe | 117/100 |
| 4,224,179 | 9/1980 | Schneider | 252/316 |
| 4,241,046 | 12/1980 | Papahadjopoulos et al. | 424/19 |
| 5,034,516 | 7/1991 | Roy et al. | 536/4.1 |
| 5,401,723 | * 3/1995 | Gaffar et al. | 514/21 |
| 5,470,829 | 11/1995 | Prisell et al. | 514/12 |
| 5,807,745 | * 9/1998 | Furie et al. | 435/375 |
| 5,843,441 | * 12/1998 | Gundel et al. | 424/143.1 |
| 5,945,102 | * 8/1999 | de Faire et al. | 424/94.63 |

FOREIGN PATENT DOCUMENTS

| | | |
|---|---|---|
| 2002218 | 5/1990 | (CA) . |
| 368 131 A2 | 5/1990 | (EP) . |
| 521 692 A2 | 1/1993 | (EP) . |
| 579 196 A1 | 1/1994 | (EP) . |
| 584 034 | 2/1994 | (EP) . |
| 589 556 A2 | 3/1994 | (EP) . |
| 63-063972 | 3/1988 | (JP) . |
| 6-166696 | 6/1994 | (JP) . |
| 6-199884 | 7/1994 | (JP) . |
| WO 91/01146 | 2/1991 | (WO) . |
| WO 92/02527 | 2/1992 | (WO) . |
| WO 93/17033 | 9/1993 | (WO) . |
| WO 93/23031 | 11/1993 | (WO) . |
| WO 94/00477 | 1/1994 | (WO) . |
| WO 94/05152 | 3/1994 | (WO) . |
| WO 94/18189 | 8/1994 | (WO) . |
| 94/22483 | * 10/1994 | (WO) . |
| WO 95/34313 | 12/1995 | (WO) . |
| WO 96/21038 | 7/1996 | (WO) . |

OTHER PUBLICATIONS

Bremer, Eric, "Glycosphingolipids as Effectors of Growth and Differentiation," *Current Topics in Membranes* 40: 387–411, 1994.

Yednak and Bremer, "Preferential Binding of the Epidermal Growth Factor Receptor to Ganglioside GM3 Coated Plates," *Molecular and Chemical Neuropathology* 21: 369–378, 1994.

Bremer et al., "Ganglioside–mediated Modulation of Cell Growth. Specific Effects of $G_{M3}$ on Tyrosine Phosphorylation of the Epidermal Growth Factor Receptor," *Journal of Biological Chemistry* 261(5): 2434–2440, 1986.

Hattori et al., "Sialyllactose–mediated Cell Interaction during Granulosa Cell Differentiation. Identification of Its Binding Proteins," *Journal of Biological Chemistry* 270(14): 7858–7863, 1995.

Hanai et al., "Ganglioside–mediated Modulation of Cell Growth. Specific Effects of $GM_3$ and Lyso–$GM_3$ in Tyrosine Phosphorylation of the Epidermal Growth Factor Receptor," *Journal of Biological Chemistry* 263(22): 10915–10921, 1988.

Aasland et al., "Expression of oncogenes in thyroid tumours: Coexpression of c–erbB2/neu and c–erbB," *Br. J. Cancer* 57: 358–363, 1988.

Aruffo et al., "CD44 Is the Principal Cell Surface Receptor for Hyaluronate," *Cell* 61: 1303–1313, 1990.

Ardvidsson et al., "Tyr–716 in the Platelet–Derived Growth Factor β–Receptor Kinase Insert Is Involved in GRB2 Binding as Ras Activation," *Molecular and Cellular Biology* 14(10): 6715–6726, 1994.

Carlsson et al., *Int. J.Radiat. Oncol. Biol. Phys.* 30(1):105–115, 1994.

Carpenter, G., "Receptors for Epidermal Growth Factor and Other Polypeptide Mitogens," *Ann. Rev. Biochem.* 56: 881–914, 1987.

Downward et al., "Close similarity of epidermal growth factor receptor and v–erb–B oncogene protein sequences," *Nature* 307: 521–527, 1984.

Glenney et al., "Monoclonal antibodies to phosphotyrosine," *Journal of Immunological Methods* 109: 277–285, 1988.

Kijima–Suda et al., "Possible Mechanism of Inhibition of Experimental Pulmonary Metastasis of Mouse Colon Adenocarcinoma 26 Sublines by a Sialic Acid: Nucleoside Conjugate," *Cancer Research* 48(13): 3728–3732, 1988.

Kim, S., "Liposomes as Carriers of Cancer Chemotherapy. Current Status and Future Prospects," *Drugs* 46(4): 618–638, 1993.

King et al., "High Throughput Assay for Inhibitors of the Epidermal Growth Factor Receptor–Associated Tyrosine Kinase," *Life Sciences* 53: 1465–1472, 1993.

(List continued on next page.)

Primary Examiner—Kathleen K. Fonda
(74) Attorney, Agent, or Firm—Seed Intellectual Property Law Group PLLC

(57) ABSTRACT

The present invention discloses carbohydrates and carbohydrate analogs that bind to epidermal growth factor (EGF) receptors. Methods of using such carbohydrates or analogs for a variety of uses related to the EGF receptor are also provided. In preferred aspects of the present invention, methods for killing or inhibiting the growth of tumor cells with increased EGF receptor activity are disclosed.

5 Claims, 7 Drawing Sheets

OTHER PUBLICATIONS

Libermann et al., "Amplification and Overpexpression of the EGF Receptor Gene in Primary Human Glioblastomas," *J. Cell Sci.* (Suppl. 3): 161–172, 1985.

Lu et al., "Amplification of the EGF Receptor and c–myc Genes in Human Esophageal Cancers," *Int. J. Cancer 42*: 502–505, 1988.

Peterson, G., "A Simplification of the Protein Assay Method of Lowry et al. Which is More Generally Applicable," *Analytical Biochemistry 83*: 346–356, 1977.

Pike et al., "Epidermal growth factor stimulates the phosphorylation of synthetic tyrosine–containing peptides by A431 cell membranes," *Proc. Natl. Acad. Sci. USA 79*: 1443–1447, 1982.

Rowlinson–Busza and Epenetos, "Targeted delivery of biologic and other antineoplastic agents," *Current Opinion in Oncology 4*: 1142–1148, 1992.

Schauer et al., "The Anti–Recognition Function of Sialic Acids: Studies with Erythrocytes and Macrophages," *Pure& Appl. Chem. 56*(7): 907–921, 1984.

Sugarman and Perez–Soler, "Liposomes in the treatment of malignancy: A clinical perspective," *Critical Reviews in Oncology/Hematology 12*(3): 231–242, 1992.

Tokovenko et al., "Inhibition of *Mycoplasma Pneumoniae* Adhesion in the Fetuinic Test Systems By Synthetic Analogues and Polymeric Forms of Neuraminic Acids," *Mikrobiolgichny Zhurnal 56*(1): 3–9, 1994.

Yarden et al., "Purification of an Active EGF Receptor Kinase with Monoclonal Antireceptor Antibodies," *Journal Biological Chemistry 260*: 315–319, 1985.

* cited by examiner

PHARMACEUTICAL COMPOSITIONS FOR TREATMENT OF EGF RECEPTOR ASSOCIATED CANCERS

CROSS-REFERENCE TO RELATED APPLICATIONS

This application is a divisional application of U.S. patent application Ser. No. 08/679,643, filed Jul. 12, 1996, now U.S. Pat. No. 6,008,203, which claimed the benefit of U.S. Provisional Application No. 60/001,150, filed Jul. 14, 1995, and abandoned.

TECHNICAL FIELD

The present invention relates generally to compounds and methods associated with the epidermal growth factor (EGF) receptor. The invention is more particularly related to carbohydrates and carbohydrate analogs that bind to EGF receptors, and methods of use therefor (e.g., to kill or inhibit the growth of tumor cells with increased EGF receptor activity).

BACKGROUND OF THE INVENTION

Growth factors are substances that induce cell proliferation, typically by binding to specific receptors on cell surfaces. One such growth factor is epidermal growth factor (EGF). EGF induces proliferation of a variety of cells in vivo, and is required for the growth of most cultured cells.

The EGF receptor is a 170–180 kD membrane-spanning glycoprotein, which is detectable on a wide variety of cell types. The extracellular N-terminal domain of the receptor is highly glycosylated and binds EGF. The cytoplasmic C-terminal domain of the receptor contains an EGF-dependent tyrosine-specific protein kinase that is capable of both autophosphorylation and the phosphorylation of other protein substrates. The two domains are connected by a single 21 amino acid hydrophobic transmembrane region. The binding of EGF to its receptor activates the receptor tyrosine kinase, which phosphorylates a variety of cellular proteins (including the EGF receptor itself). This phosphorylation initiates a signal transduction pathway that ultimately leads to DNA replication, RNA and protein synthesis, and cell division. EGF also induces the concentration of the receptor into clathrin-coated pits, internalization into intracellular vesicles, and finally degradation in the lysosomes.

The amplification or overexpression of the EGF receptor is associated with the uncontrolled cell division of many cancers. Published studies support a role for the EGF receptor in cell transformation and maintenance of the transformed phenotype. There is also a high level of sequence homology between the EGF receptor and the avian v-erbB oncogene product. In addition, overexpression of the EGF receptor has been shown to result in the EGF-dependent transformation of NIH 3T3 cells.

Many tumors of mesodermal and ectodermal origin overexpress the EGF receptor. For example, the EGF receptor has been shown to be overexpressed in many gliomas, squamous cell carcinomas, breast carcinomas, melanomas, invasive bladder carcinomas and esophageal cancers. In addition, studies with primary human mammary tumors have shown a correlation between high EGF receptor expression and the presence of metastases, higher rates of proliferation, and shorter patient survival.

Attempts to exploit the EGF receptor system for anti-tumor therapy have generally involved the use of monoclonal antibodies against the EGF receptor. However, this approach has serious drawbacks. The monoclonal antibodies developed to date are effective inhibitors of cell growth in only some of the existing cancer cell lines. In addition, studies with athymic mouse xenografts suggest that therapeutic intervention with anti-receptor antibodies will require prolonged exposure, which may result in the generation of antibodies against the anti-receptor antibodies in the patient. Thus, to date, no successful anti-tumor therapies exploiting the EGF receptor system have been developed.

Accordingly, there is a need in the art for improved compounds and methods for treating EGF-receptor associated cancers. The present invention fulfills this need and provides further related advantages.

SUMMARY OF THE INVENTION

Briefly stated, this invention provides compounds and methods related to the epidermal growth factor (EGF) receptor. In one aspect of the invention, compounds are provided, having the formula X-Y-Z-R, wherein X is a sialic acid or a non-saccharide group that mimics the structure of a sialic acid group, Y and Z are independently a monosaccharide residue or a non-saccharide group that mimics the structure of a monosaccharide residue, and R is hydrogen or a carrier group, with the proviso that where X is a sialic acid group, Y and Z respectively are not the following: galactose and glucose, galactose and N-acetylglucosamine, galactose and galactose, galactose and N-acetylgalactosamine, sialic acid and sialic acid, sialic acid and galactose, N-acetylgalactosamine and galactose, N-acetylgalactosamine and N-acetylglucosamine, or N-acetylglucosamine and galactose. In an embodiment, X is a sialic acid group or a 2-hydroxyacetic acid group, Y is a galactose group or a cyclohexane group, Z is a glucose group, a cyclohexane group or an N-acetylglucosamine group, and R is hydrogen or a carrier group, with the proviso that where X is a sialic acid group and Y is a galactose group, then Z is not a glucose group or an N-acetylglucosamine group.

In a related embodiment, the present invention provides compositions comprising a liposome that includes a compound as described above or a carbohydrate compound having a type 2 saccharide chain without a sialic acid residue or an analog thereof, wherein said compound contains a carrier group. In an embodiment, the compound has the formula LNnT-C, wherein LNnT is a lacto-N-neotetraose group and C is a carrier group.

In another aspect, pharmaceutical compositions are provided, comprising: (a) a compound as described above or a carbohydrate compound having a type 2 saccharide chain without a sialic acid residue or an analog thereof; and (b) a pharmaceutically acceptable carrier or diluent. In an embodiment, the compound has the formula LNnT-C, wherein LNnT is a lacto-N-neotetraose group and C is a carrier group.

In another aspect of the invention, methods are provided for purifying an EGF receptor, comprising: (a) contacting a preparation containing an EGF receptor with a sialylated lactose carbohydrate compound, a carbohydrate compound having a type 2 saccharide chain without a sialic acid residue, or an analog of either, wherein said compound is immobilized on a solid support, and wherein said contacting takes place under conditions such that said EGF receptor binds to said immobilized compound; (b) separating the preparation from the immobilized compound, wherein the EGF receptor remains bound to the immobilized compound;

and (c) isolating the bound EGF receptor from the immobilized compound.

In a further aspect of this invention, methods are provided for screening for a candidate molecule able to bind to an EGF receptor, comprising: (a) contacting an EGF receptor immobilized on a solid support with a candidate molecule and with a sialylated lactose carbohydrate compound, a carbohydrate compound having a type 2 saccharide chain without a sialic acid residue, or an analog of either; (b) separating unbound compound from the immobilized EGF receptor; and (c) detecting compound bound to the immobilized EGF receptor. In another embodiment, the method for screening comprises: (a) contacting a compound immobilized on a solid support with a candidate molecule and with an EGF receptor, wherein said compound is a sialylated lactose carbohydrate compound, a carbohydrate compound having a type 2 saccharide chain without a sialic acid residue, or an analog of either; (b) separating unbound EGF receptor from said immobilized compound; and (c) detecting EGF receptor bound to said immobilized compound, therefrom determining whether said candidate molecule binds to said EGF receptor.

In yet another aspect, this invention provides methods for inhibiting EGF receptor kinase activity comprising contacting an EGF receptor with a sialylated lactose carbohydrate compound, a carbohydrate compound having a type 2 saccharide chain without a sialic acid residue, or an analog of either. In an embodiment, the compound has the formula LNnT-R, wherein LNnT is a lacto-N-neotetraose group and R is hydrogen or a carrier group.

In a related aspect, methods are provided for inhibiting tumor cell growth within a biological preparation, comprising contacting a biological preparation with a sialylated lactose carbohydrate compound, a carbohydrate compound having a type 2 saccharide chain without a sialic acid residue, or an analog of either. In an embodiment, the compound has the formula LNnT-R, wherein LNnT is a lacto-N-neotetraose group and R is hydrogen or a carrier group.

In a further related aspect, methods are provided for killing tumor cells in a biological preparation, comprising contacting a biological preparation with a sialylated lactose carbohydrate compound, a carbohydrate compound having a type 2 saccharide chain without a sialic acid residue, or an analog of either. In an embodiment, the compound has the formula LNnT-C, wherein LNnT is a lacto-N-neotetraose group and C is a carrier group.

In yet another aspect, the present invention provides methods for inhibiting growth, in a warm-blooded animal, of a tumor cell for which an EGF receptor is associated, comprising administering in an amount effective to inhibit growth of said tumor cell a sialylated lactose carbohydrate compound, a carbohydrate compound having a type 2 saccharide chain without a sialic acid residue, or an analog of either. In an embodiment, the compound has the formula LNnT-R, wherein LNnT is a lacto-N-neotetraose group and R is hydrogen or a carrier group.

In a related aspect, this invention provides methods for killing, in a warm-blooded animal, a tumor cell for which an EGF receptor is associated, comprising administering in an amount effective to kill said tumor cell a sialylated lactose carbohydrate compound, a carbohydrate compound having a type 2 saccharide chain without a sialic acid residue, or an analog of either. In an embodiment, the compound has the formula LNnT-C, wherein LNnT is a lacto-N-neotetraose group and C is a carrier group.

These and other aspects of the present invention will become apparent upon reference to the following detailed description and attached drawings.

DETAILED DESCRIPTION OF THE INVENTION

Figure 1:
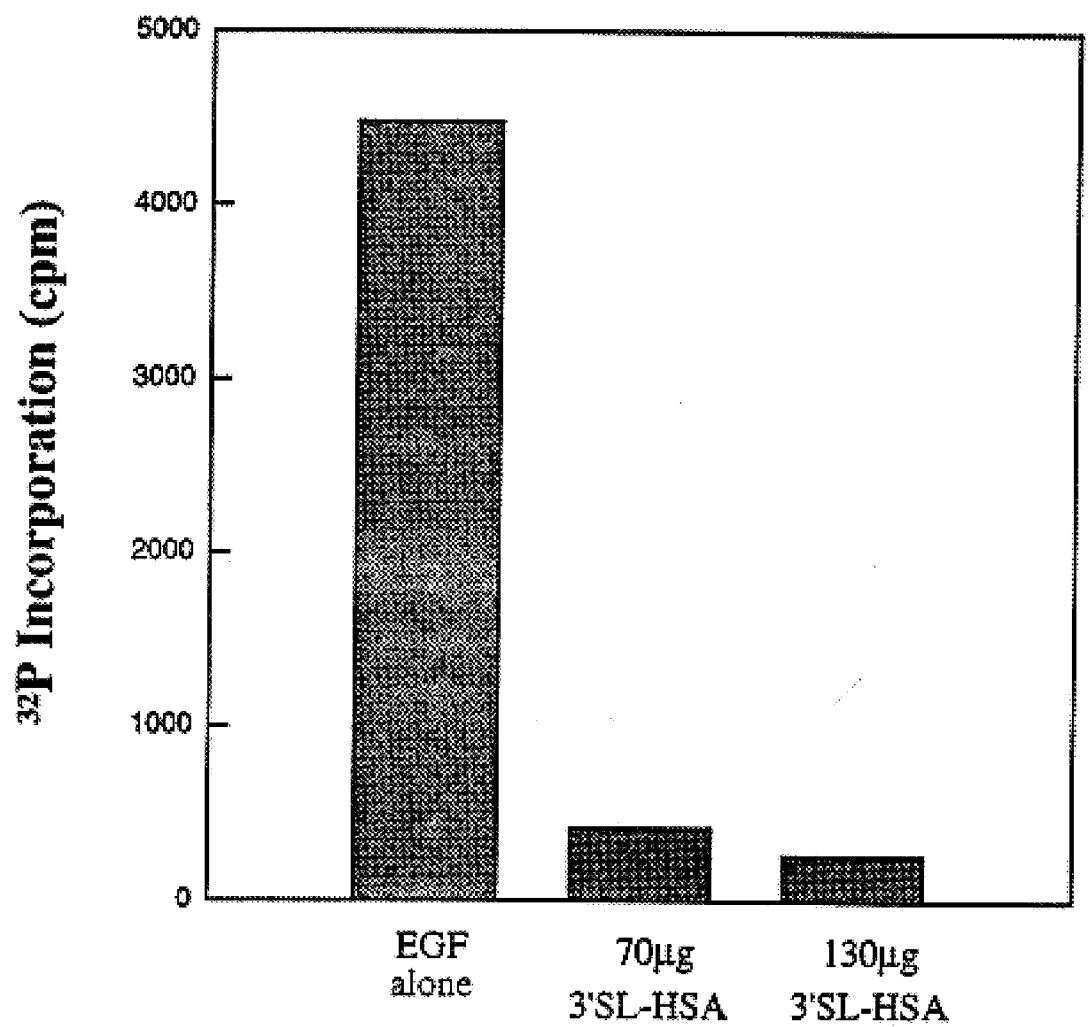
FIG. 1 illustrates the inhibition of EGF receptor autophosphorylation by 3' SL-HSA.

Prior to setting forth the invention, it may be helpful to an understanding thereof to set forth definitions of certain terms to be used hereinafter. In the context of this invention, a "carbohydrate" is a compound containing one or more monosaccharide residues. "Monosaccharides" include unsubstituted, nonhydrolyzable saccharides such as glucose or galactose, as well as modified, nonhydrolyzable saccharides in which one or more hydroxyl groups contain substitutions or have been replaced with hydrogen or substituted carbon atoms. One such substituted monosaccharide is sialic acid. In the context of this invention, an "EGF receptor" includes the entire protein, its extracellular domain and any portion of the protein able to bind EGF.

Portions of a carbohydrate molecule may consist of non-saccharide groups. In particular, groups such as cyclohexane that mimic the structure of a monosaccharide residue may be present. A "carbohydrate analog," in the context of this invention, is a compound that has a three dimensional structure similar to that of a carbohydrate, but that contains few or no monosaccharide residues. Three dimensional structures may be determined using computer modeling programs such as, for example, the model of Hricouini et al., *Biochem.* 31:10018–10023 (1992). In particular, carbohydrates and carbohydrate analogs may contain groups such as anti-idiotypic antibodies or cyclohexane derivatives that mimic the structure of a monosaccharide residue.

Non-saccharide carrier groups may also be present within compounds of this invention. A "carrier group" is any group that facilitates the transport, binding or activity of a compound (i.e., a carbohydrate or carbohydrate analog). For example, a carrier group may facilitate incorporation of a compound into a cell membrane or liposome, or may improve the binding of a compound to an EGF receptor. In another example, a multivalent presentation of a compound may increase the compound's conjugate exponentially by increasing its avidity for the EGF receptor. A carrier group may also, or alternatively, kill the cell to which the compound binds. Such carrier groups include, for example, cytotoxic agents, toxins, radionuclides, and prodrugs. A "conjugate," in the context of this invention, is any carbohydrate or carbohydrate analog that contains a carrier group.

As noted above, the present invention is generally directed to compounds and methods associated with the EGF receptor (including, for example, killing or inhibiting the growth of tumor cells in EGF receptor-associated cancers). In one embodiment, the compounds of the present invention are members of the sialylated lactose series (including both type 1 and type 2 chains, and including derivatives) or analogs thereof. Type 1 and type 2 chains refer to polylactosamine unit structures, i.e., Galβ1→3/4GlcNAc. The polylactosamine having the Galβ1→3GlcNAc structure is called the type 1 chain, and that having the Galβ1→4GlcNAc structure is referred to as the type 2 chain. Examples of type 1 and type 2 chains are known to those in the art. In another embodiment, the compounds useful in this invention are carbohydrates having type 2 saccharide chains without a sialic acid residue, including derivatives thereof such as lacto-N-neotetraose (i.e., LNnT or Galβ1-4GlcNAcβ1-3Galβ1-4Glc). Such compounds may be used, for example, to treat EGF receptor-associated cancers, to purify EGF receptors and to identify additional EGF receptor-binding compounds.

The compounds of this invention that are members of the sialylated lactose series (and derivatives) or analogs thereof may be generally represented by the following formula:

X-Y-Z-R wherein X is a sialic acid group or a non-saccharide group that mimics the structure of a sialic acid group, Y and Z represent monosaccharide residues or non-saccharide groups that mimic the structure of a monosaccharide residue and R is hydrogen or a carrier group. Preferably, X is a sialic acid group or a 2-hydroxyacetic acid group, Y is a galactose group or a cyclohexane group and Z is a glucose group, a cyclohexane group or a N-acetylglucosamine group.

In the embodiments in which R is hydrogen, such compounds may generally be represented by the formula:

X-Y-Z wherein X, Y and Z are as recited above. Such compounds include, but are not limited to, 3'-sialyllactose (i.e., Neu5Acα2-3Galβ1-4Glc), 6'sialyllactose (i.e., Neu5Acα2-6Galβ1-4Glc) and LSTa (i.e., Neu5Acα2-3Galβ1-3GlcNAcβ1-3Galβ1-4Glc), as well as the following carbohydrates:

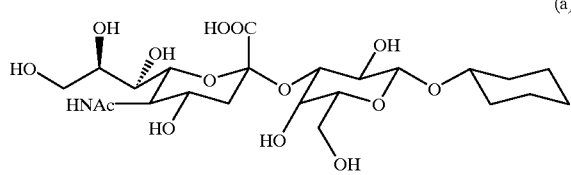

(a)

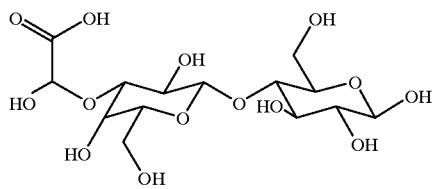

(b)

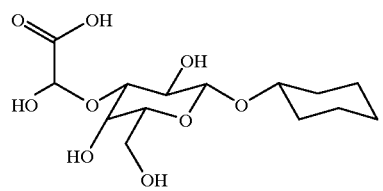

(c)

In the embodiments in which R is a carrier group, the members of the sialylated lactose series (including derivatives) or analogs thereof may generally be represented by the formula:

X-Y-Z-C wherein X, Y and Z are as recited above, and C may be any carrier group. In one preferred embodiment, C is a hydrophobic carrier group that allows incorporation of the compound into a liposome. Such groups include serum albumin (such as bovine serum albumin or human serum albumin), ceramide, lipids (such as dipalmitoylphosphatidylcholine), cholesterol and long aliphatic chains (e.g., chains containing 8–25 carbon atoms in the backbone). In another preferred embodiment, C is an agent capable of killing cells to which the conjugate binds. For example, C may be a cytotoxic agent (e.g., daunomycin, doxorubicin, neocarzinostatin or vindesine), a toxin (e.g., ricin A or a ribosome-inactivating protein such as saporin), a radionuclide (e.g., a radioactive form of iodine or rhenium), a "prodrug" (i.e., a group that is not itself toxic to the cell, but that can be rendered toxic after binding of the conjugate to the EGF receptor by the addition of a second activating compound) or an enzyme that can convert a prodrug into an active drug. Suitable prodrugs include boron, doxifluridine, or the prodrug precursor of palytoxin. The enzyme may be, for example, beta-lactamase, cytosine deaminase or nitroreductase, which can be used in conjunction with an appropriate prodrug.

In yet another preferred embodiment, C is an artificial polymer (i.e., a polymer that is not known to be found in nature). Suitable artificial polymers include polyacrylamide, and derivatives thereof, polylysine and dendrimers (as described, for example, in Tomalia, *Scientific American* (May, 1995) at 62–66). More preferably, the carrier group is multivalent (i.e., capable of binding to more than one carbohydrate or carbohydrate analog molecule) or is capable of forming an aggregate structure of carrier groups. Such carrier groups have the advantage of increasing the local concentration of the non-carrier portion of the carbohydrate. The above carrier groups may also be incorporated into carbohydrates containing a type 2 saccharide chain without a sialic acid residue, such as lacto-N-neotetraose (LNnT), as described above.

The conjugates of this invention may generally be prepared by coupling a carbohydrate, such as 3'sialyllactose, or a carbohydrate analog to a carrier by any of a variety of means known to those in the art. In one such method, a linker such as 2-(4-aminophenyl)ethylamine (APEA) or p-trifluoroacetamidoaniline (which may be synthesized from p-nitroaniline and trifluoroacetic anhydride, followed by reductive hydrogenation) may be used. Such linkers react with the reducing end of the carbohydrate by reductive amination, and may be converted to an isothiocyanate derivative by reacting with thiophosgene. This compound is highly reactive with amines, and will couple to compounds such as proteins, phosphatidyl ethanolamine and amino groups in dendrimers and peptides. The use of such linkers has the advantages of simplicity, stability, high yield and compatibility with sialyloligosaccharides. Polylactosamine chains of varying lengths may generally be prepared according to the method of Srivastava et al., *J. Carbohydrate Chem.* 10:927–933 (1991), and sialylated according to the method of De Vries and van den Eijnden, *Biochem.* 33:9937–9944 (1994). Of course, the above descriptions are provided solely for exemplary purposes, and other linking methods will be readily apparent to those in the art.

Conjugates of this invention may be incorporated into liposomes. Liposomes are spherical structures that contain, for example, a lipid bilayer surrounding an aqueous interior. The liposome structure is maintained, in part, by van der Waals interactions between the hydrophobic portions of the lipids. Accordingly, conjugates that contain an appropriate hydrophobic carrier group, as described above, may be incorporated into the lipid bilayer of the liposome. A cytotoxic agent or drug may then be encapsulated in the liposome, for delivery to cells that contain an EGF receptor. Representative examples of the uses and pharmaceutical compositions of liposomes for cancer chemotherapy are described in Kim, *Drugs* 46(4):618–638 (1993). In general, incorporation of a conjugate into a liposome may be achieved by combining the conjugate, cholesterol, a lipid (such as dipalmitoylphosphatidylcholine) and a solvent in suitable proportions, and allowing the mixture to dry. Upon the addition of phosphate buffered saline and sonication, liposomes of various sizes are formed. The liposomes may be prepared and size-selected (e.g., with one or more filters) using any of a variety of procedures known to those of ordinary skill in the art, such as (for example) the methods described in U.S. Pat. Nos. 4,241,046 and 4,224,179, and references cited therein.

As noted above, the compounds of this invention may be used for a variety of purposes, including for the purification of EGF receptors, for the screening compounds having the ability to bind to EGF receptor and for the inhibition of EGF receptor kinase activity. Such compounds may also be used to inhibit tumor cell growth or to kill tumor cells, either within a biological preparation or in a warm-blooded animal. The term "biological preparation," in the context of this invention, encompasses body samples, cell samples and fractions thereof. Body samples include urine, cervical secretions, bronchial aspirates (including bronchial washings), sputum, saliva, feces, serum, umbilical cord blood, synovial and cerebrospinal fluid, nipple aspirates and ascites. Cell samples include tissue samples, as well as cell cultures and suspensions, and cellular components such as membranes. Preferred cell samples are those samples that contain cultured or isolated bone marrow cells or peripheral blood stem cells or umbilical cord blood cells.

In one aspect, the compounds of this invention may be used to purify an EGF receptor from any appropriate biological preparation. For example, EGF receptor may be purified from preparations of membrane proteins obtained from suitable cultured cells, such as A431 cells. EGF receptor that is purified in this manner may be naturally-occurring or recombinant.

Typically, purification of EGF receptor may be achieved using a carbohydrate or carbohydrate analog that has been immobilized on a solid support. Suitable support materials include, but are not limited to, chromatography support materials, glass beads, polymeric matrices, plastics (such as latex, polystyrene or polyvinylchloride), sintered glass discs, fiberglass membranes, polymeric membranes and magnetic particles. Magnetic particles may contain a thermoplastic resin combined with a magnetically responsive powder, and coated with a polymer having reactive functional groups. Such particles are disclosed, for example, in U.S. Pat. No. 5,200,270. Alternatively, magnetic particles may contain a magnetic metal oxide coated with a polymer (such as a polysaccharide or a silane) having pendant functional groups for binding the carbohydrate or carbohydrate analog, as disclosed, for example, in U.S. Pat. Nos. 4,452,773; 4,661,408; 4,695,393 and 5,169,754. The particles may also have a metal oxide surface (with a metal or polymer core) to which the carbohydrate or carbohydrate analog is directly bound, by the methodology disclosed, for example, in U.S. Pat. Nos. 4,018,886 and 5,320,944. Other suitable particles will be apparent to those of ordinary skill in the art.

The carbohydrate or carbohydrate analog may be immobilized on the support using a variety of techniques known to those of ordinary skill in the art. In the context of the present invention, the term "immobilization" refers to both covalent attachment (which may be a direct linkage between the carbohydrate or carbohydrate analog and functional groups on the support, or which may be a linkage by way of a cross-linking agent) and noncovalent association, such as adsorption. Briefly, covalent attachment may be achieved by first reacting the support with a bifunctional reagent (see, e.g., catalog of Pierce Chemical Co., Rockford, Ill.), such as benzoquinone, that will react with both the support and a functional group, generally a hydroxyl group, on the carbohydrate or carbohydrate analog. Alternatively, the carbohydrate or carbohydrate analog may be immobilized on a support by condensation of an aldehyde group on the support with an amine and an active hydrogen on the carbohydrate or analog (e.g., in a Mannich reaction).

The carbohydrate or carbohydrate analog is preferably immobilized by adsorption to a support, using any of a variety of techniques. For example, a conjugate that includes a suitable carrier, such as bovine serum albumin (BSA) or the constant portion of the heavy chain of gamma immunoglobulin, may be physically adsorbed to appropriate surfaces of particles or other solid supports by contacting the conjugate with the support for a suitable amount of time. The contact time varies with temperature, but is typically between about 1 hour and 1 day. Following adsorption, the coated support is typically incubated with a blocking agent, such as bovine serum albumin in phosphate buffered saline, to block non-specific binding to the support.

The immobilized conjugate may then be contacted with the preparation containing EGF receptor for an incubation time and under conditions that permit binding of the EGF receptor to the immobilized conjugate. Suitable conditions will be apparent to those of ordinary skill in the art. In general, physiological conditions (e.g., phosphate-buffered saline) are appropriate.

After incubation, the support to which EGF is bound may be separated from the remainder of the preparation and washed to remove contaminants. The substantially pure EGF receptor may then be removed from the support in a suitable eluent, and analyzed to confirm the presence of active EGF receptor. Such analyses may be performed using a variety of techniques known to those of ordinary skill in the art, including the method of King et al., *Life Sciences* 53:1465–1472 (1993). EGF receptor purified in this manner may be detected as a single 170–180 kD band using SDS-PAGE. No other kinase activity is detectable (i.e., no other phosphorylated proteins are detected).

The compounds of this invention may also be used to screen candidate molecules for the ability to bind to EGF receptor. In one embodiment, the screen is performed using a competition assay. Briefly, in this embodiment, EGF receptor is immobilized on a support and incubated with both the candidate molecule and a carbohydrate or carbohydrate analog. After incubation, the unbound compounds are removed, and the bound carbohydrate or carbohydrate analog is detected using a reporter group. Typical reporter groups include radioisotopes (such as tritium), fluorescent groups, luminescent groups, enzymes (such as horseradish peroxidase or alkaline phosphatase), substrates, cofactors, inhibitors, biotin and dye particles. The reporter group may be linked to the carbohydrate or carbohydrate analog, or to a separate molecule that binds to the carbohydrate or analog. In either case, the amount of bound reporter group detected is inversely related to the amount of bound candidate molecule (i.e., a lower amount of bound reporter group indicates that the candidate molecule has a greater ability to bind to the EGF receptor).

In general, EGF receptor may be immobilized directly on any appropriate support, such as the well of a microtiter plate or other support described above. Alternatively, an anti-EGF receptor antibody (which may be prepared using techniques well known to those of ordinary skill in the art) may be immobilized on the support, and EGF receptor may be bound to the immobilized antibody. Immobilization of EGF receptor or anti-EGF receptor antibody may generally be achieved by the methods described above for the immobilization of carbohydrates.

The carbohydrate or carbohydrate analog employed in this method may, but need not, contain a carrier group. In addition, as discussed above, the carbohydrate or analog may contain a reporter group. Reporter groups may be incorporated by any of a variety of techniques known to those in the art (see, e.g., catalog of Pierce Chemical Co., Rockford, Ill.). For example, tritium may be incorporated using sodium borohydride (see, e.g., catalog of Oxford GlycoSystems, Rosedale, N.Y.). Reporter groups may also be linked via a spacer arm (e.g., APD or APEA) that is joined to the carbohydrate or carbohydrate analog by reductive amination.

The immobilized EGF receptor is incubated with the candidate molecule and the carbohydrate or carbohydrate analog to allow the binding reactions to approach equilibrium. An optimal incubation time may be determined by measuring the time dependence of binding, and selecting a time at which an appropriate percentage (e.g., 95%) of maximum binding has been achieved. Unbound molecules are then removed from the support by separation (e.g., by filtration), optionally followed by an appropriate wash. If the carbohydrate or carbohydrate analog contains a reporter group, the reporter group may then be detected. Radioactive reporter groups may be detected using, for example, scintillation counting. Fluorescent groups may be detected using, for example, fluorometric techniques. Spectroscopic methods may be used to detect dyes and luminescent groups. Biotin may be detected using, for example, streptavidin coupled to a reporter group (commonly a radioactive or fluorescent group or an enzyme). Enzyme reporter groups may generally be detected by addition of substrate (generally for a specific period of time), followed by spectroscopic or other analysis of the reaction products.

Alternatively, if the reporter group is bound to a molecule (such as an antibody, lectin or other carbohydrate binding protein) that is capable of binding to the carbohydrate or carbohydrate analog, the molecule containing the reporter group may be added to the immobilized EGF receptor after removal of the unbound carbohydrate or carbohydrate analog, and incubated for an appropriate period of time. Suitable reporter groups for antibodies include radioisotopes, such as radioactive iodine, and other groups described above. The incubation time may be optimized by evaluating the time dependence of binding. After incubation, the unbound antibody is removed prior to detection of the reporter group, as described above. In this manner, the bound carbohydrate or carbohydrate analog may be detected indirectly, based on the level of the bound antibody.

In another embodiment of the screening for candidate molecules, a variation on the competition assay described above may be used. It will be evident to those in the art that portions of the above discussion are applicable to this embodiment as well. Briefly, in this embodiment, a carbohydrate compound or analog thereof is immobilized on a support and incubated with both the candidate molecule and EGF receptor. After incubation, the unbound EGF receptor is removed, and the bound EGF receptor is detected. For example, an antibody which is against EGF receptor and which possesses a reporter group may be used. Alternatively, a second antibody which is against the anti-EGF receptor antibody and which contains a reporter group may be used. Other examples of alternative detection methodologies are described above.

In another embodiment, the screen for candidate molecules having the ability to bind to an EGF receptor is a direct assay. In this embodiment, the molecule to be tested is immobilized on a support, such as the well of a microtiter plate, as described above. EGF receptor (which may be purified as described above) is then allowed to bind to the immobilized candidate molecule. The EGF receptor may be linked to a reporter group, or may be detected using an anti-EGF receptor antibody to which a reporter group is linked, as described above. In this embodiment, a higher level of reporter group detected indicates a molecule with a greater ability to bind to an EGF receptor.

Within other aspects, the compounds of this invention may be used to inhibit EGF receptor kinase activity, to inhibit tumor cell growth and/or to kill tumor cells in biological preparations or in warm-blooded animals, preferably humans. Suitable biological preparations for inhibiting EGF receptor kinase activity are any preparations that contain EGF receptors (e.g., preparations of membrane proteins from cell lines such as A431 (ATCC No. CRL 1555), U118-MG (ATCC No. HTB15), and/or U373-MG (ATCC No. HTB17)). For inhibiting tumor cell growth or killing tumor cells, suitable biological preparations and warm-blooded animals are those that contain tumor cells that express EGF receptor (i.e., tumor cells with which EGF receptor is associated).

In one such aspect, inhibition of kinase activity may generally be achieved by contacting an appropriate amount of a compound as described above with EGF receptor, either in vitro or in vivo. For example, the kinase activity of EGF receptor within a biological preparation may be inhibited by combining a suitable amount of carbohydrate or carbohydrate analog with the biological preparation. Kinase activity may be measured by incubating the EGF receptor with a test peptide (such as the RR-src peptide, which contains a single tyrosine residue) and radiolabeled ATP, and measuring the amount of label incorporated into the test peptide using, for example, a liquid scintillation counter. Alternatively, autophosphorylation of the EGF receptor in intact cells may be measured with anti-phosphotyrosine antibody, as described in Arvidsson et al., *Mol. Cell. Biol.* 14:6715 (1994) or Glenney et al., *J. Immun. Meth.* 109:277 (1988). Kinase activity of EGF receptor in a warm-blooded animal may generally be inhibited by administration of an effective amount of the carbohydrate or carbohydrate analog to the animal.

For inhibiting kinase activity, without killing the target cell, the compound may be any of the carbohydrates or carbohydrate analogs described above. In preferred embodiments, the compound is a conjugate. However, if cell survival is desired, the use of carrier groups that kill the target cell should be avoided.

For administration to warm-blooded animals, the carbohydrate or carbohydrate analog may be combined with a pharmaceutically acceptable carrier or diluent to form a pharmaceutical composition. Any of a variety of carriers or diluents may be employed. Liquid diluents include, for example, water, saline, dextrose, glycerol, ethanol and combinations thereof. For solid pharmaceutical compositions, suitable carriers include pharmaceutical grades of mannitol, lactose, starch, magnesium stearate, cellulose, magnesium carbonate and the like. Pharmaceutical compositions may also contain one or more binders (such as gelatin, acacia or corn starch), sweeteners (e.g., lactose, sucrose or saccharin), flavoring agents (e.g., oil of wintergreen, peppermint or fruit flavors), lubricants (e.g., magnesium stearate) and/or excipients (e.g., dicalcium phosphate). The pharmaceutical composition may take a variety of forms, including tablets, capsules, powders, granules, emulsions, ointments, gels, foams or aerosols. In addition, the carbohydrate in the pharmaceutical composition may be incorporated into a liposome. Administration may be by any means sufficient to expose the desired region of the animal to the carbohydrate or carbohydrate analog, including oral administration, inhalation, and injection (e.g., intravenous, intracutaneous, intramuscular or subcutaneous).

An effective amount of carbohydrate or carbohydrate analog may be determined using methods known to those of ordinary skill in the art. Specifically, dose response curves may be used to determine an effective amount for inhibiting EGF receptor activity within a biological preparation, preferably without causing significant cell death. Dose response curves may also be generated in animals. An appropriate amount for treatment of humans may be determined by extrapolating from animal data or in vitro data, and/or using clinical trials. Suitable doses and courses of treatment depend upon a variety of factors, including the specific compound used, the size of the patient and the method of administration. A suitable amount of the compound for administration to a warm-blooded animal will be up to and including the highest therapeutic dose that does not cause unacceptable side effects or toxicity (as determined in animal models, followed by clinical trials). In general, a suitable dose of carbohydrate or carbohydrate analog is an amount sufficient to raise the blood concentration of carbohydrate or carbohydrate analog to $10^{-15}$ to $10^{-2}$ M. Doses may be administered once or several times per day.

To inhibit tumor cell growth in a biological preparation or a warm-blooded animal, an appropriate amount of a compound as described above is contacted with tumor cells containing EGF receptors. Tumor cell growth in a biological preparation may be inhibited by incubating an appropriate amount of the compound with the biological preparation. Similarly, the growth of in vivo tumors may generally be inhibited by administering an effective amount of the compound to the affected warm-blooded animal by any of the methods described above.

If, in this aspect, a conjugate is employed, and cell survival is desired, any of the above carriers that are not lethal to the target cell may be employed. Suitable amounts of carbohydrate or carbohydrate analog may generally be determined, as described above, using dose response curves and by evaluating the time dependence of the response. For tumors in a warm-blooded animal, the compound generally may be administered to the animal as discussed above.

The compounds of this invention may also be used to kill tumor cells in a biological preparation or in a warm-blooded animal. In one embodiment, a conjugate is employed that contains a carrier group capable of killing the cell, such as a cytotoxic agent, a toxin, a radionuclide (e.g., radioactive iodine), a prodrug, or an enzyme that converts a prodrug to an active drug, as described above. Alternatively, a conjugate may be incorporated into a liposome, as described above, and the cytotoxic agent, prodrug or other agent capable of killing the cell may be encapsulated in the liposome for delivery to the tumor cell. Any appropriate agent known to those of ordinary skill in the art may be used for this purpose.

Tumor cells in a biological preparation may be killed by incubating the conjugate with the biological preparation. A suitable amount of conjugate and an appropriate incubation time may generally be determined, as described above, using dose response curves and by evaluating the time dependence of the response.

In this embodiment, the biological preparation preferably contains bone marrow cells, and the incubation takes place prior to autologous bone marrow transplantation. Bone marrow cells may be isolated by any of a variety of techniques known to those of ordinary skill in the art. For example, commercially available kits, such as CEPRATE (CellPro, Inc., Bothell, Wash.) may be used according to the manufacturer's instructions. The bone marrow cells are incubated with the conjugate for an amount of time sufficient to kill the cancer cells, but under conditions that will maintain the viability and proliferative potential of the bone marrow cells. Such conditions may be determined by dose response curves, as discussed above. For killing tumor cells in a warm-blooded animal, the conjugate is preferably administered in the form of a pharmaceutical composition, as described above.

A sialylated lactose carbohydrate compound, a carbohydrate compound having a type 2 saccharide chain without a sialic acid residue, or an analog of either, may be used alone or in combination (e.g., with one another and/or with one or more other compounds) in the preparation or manufacture of a medicament. Such medicaments may be for a variety of uses, including for the inhibition of tumor cell growth or for killing tumor cells (e.g., where a tumor cell has increased EGF receptor activity) such as for the treatment of EGF receptor associated cancers.

The following Examples are offered by way of illustration and not by way of limitation.

EXAMPLES

Example 1

Synthesis of Carbohydrate Conjugates

This Example illustrates the synthesis of carbohydrates and carbohydrate analog conjugates.

A. Conjugation to Serum Albumin via APD

Carbohydrates and carbohydrate analogs may be coupled to human serum albumin by way of aminophenylene diamine (APD) as described below for 3'-sialyllactose (3'SL). The carbohydrate portions of these conjugates may be obtained from commercial sources such as GlycoTech Corp., Gaithersburg, Md. or Oxford GlycoSystems, Rosedale, N.Y.

The APD linker arm is derived from p-trifluoroacetamidoaniline (TFAN), which is synthesized from 4-trifluoroacetamidonitrobenzene. 2.76 g of p-nitroaniline is dissolved in 25 ml of redistilled pyridine, and the dark yellow solution is cooled in an ice bath. 5 ml of trifluoroacetic anhydride is added dropwise to the solution under constant stirring. The solution is then filtered on a sintered glass filter and washed with cold water. The solid material is recrystallized by adding approximately 100 ml of ethanol and gradually adding an additional 50 ml of ethanol while heating to 60° C. under stirring. The solution is covered and placed in the refrigerator overnight for recrystallization.

The solution is refiltered on a sintered glass filter, and the crystals are washed with cold water and dried under high vacuum. Yield of 4-trifluoroacetamidonitrobenzene is about 90–92% and the melting point is 140° C. The crystals are stored under desiccation at −20° C. or immediately subjected to reductive hydrogenation.

Reductive hydrogenation is achieved by adding 2 grams of 4-trifluoroacetamidonitrobenzene to 50 mg of palladium on activated charcoal in 30 ml of ethanol. Hydrogen gas is bubbled in the solution at room temperature for 3 hr. The solution is then filtered on Whatman No. 1 paper to remove the charcoal. The filter is washed with ethanol and the filtrate is pooled with the washing and evaporated to dryness by rotary evaporation. The product is crystallized by dissolving the residue in 20–40 ml of ethyl ether. Hexane is gradually added and the light pink crystals are collected by filtration and washed with hexane. The resulting 4-trifluoroacetamidoaniline (TFAN) has a melting point of 118° C. and a yield of 76%.

TFAN is used to couple oligosaccharides such as 3'sialyllactose to amine-containing proteins such as serum albumin. In the first step of the reaction, the oligosaccharide is coupled to TFAN by reductive amination followed by acetylation. 2 mg of 3'sialyllactose is added to 10 mg of TFAN in 0.3 ml of ethanol/water 2:1 (v/v). 0.02 ml of glacial acetic acid and 6 mg of $NaCNBH_3$ is added under stirring. The glass vial is capped and incubated under stirring at 30° C. for 15–20 hr. The reaction is monitored by TLC, as described below.

0.05 ml of acetic anhydride is added and incubated at 30° C. for an additional 3 hr. The reaction is monitored for complete acetylation by TLC. The reaction is then transferred to a 13×100 mm glass test tube with a PTFE lined screw cap. 5 ml of ethyl acetate is added, followed by 5 ml of water for extraction. The phases are separated and the water phase is washed with another 5 ml of ethyl acetate. The water phases are combined and concentrated to 1–2 ml by rotary evaporation.

The concentrate is applied to a $C_{18}$ column (4×0.4 mm i.d.) preconditioned with methanol followed by water. After washing with 5 column volumes of water, the N-acetylated TFAN derivative of 3'sialyllactose is eluted with 5 column volumes of methanol. The sample is evaporated to dryness by rotary evaporation.

The second step of the reaction removes the trifluoro group from the nitrogen. The dry TFAN derivative is dissolved in 0.5 ml of 0.5 M NaOH and incubated at room temperature for 3 hr. The reaction is monitored by TLC.

The third step of the reaction converts the amine to an isothiocyanate. 1 ml of ethanol is added to the reaction, followed by 0.02 ml glacial acetic acid. The pH is adjusted to about 7 with 0.1 ml of 0.2 M NaOH. Under constant stirring, 0.004 ml of thiophosgene is carefully added. The pH is adjusted to above 5 with another 0.1 ml of 0.2 M NaOH. Conversion of the aromatic amine to the isothiocyanate is almost instantaneous.

The reaction product is extracted with 0.5 ml water and 1 ml ethyl ether. The upper phase (ether) is washed again with 0.5 ml water. The water phases are combined and rotary evaporated to 0.5–1 ml.

The last step of the reaction couples the isothiocyanate derivative to the amine-containing carrier molecule, such as serum albumin. The isothiocyanate derivative is transferred to a 5 ml vial containing 5 mg of human serum albumin in 0.1 M borate buffer at pH 9.4. The pH of the solution is readjusted to 9.4 with 0.5 M NaOH. The reaction is incubated under constant stirring at room temperature for at least 20 hr, and is monitored by TLC. The reaction is then dialyzed against three changes of 20 mM $NH_4HCO_3$, lyophilized and the degree of coupling is characterized by using standard assays for protein and sialic acid.

The TLC analyses described above are performed on silica gel 60 HPTLC thin layer plates in ethyl acetate/methanol/acetic acid/water, 6:3:3:2 (v/v/v/v). The Rf values are as follows:

| Compound | Rf Value |
| --- | --- |
| 3'SL | 0.22 |
| 3'SL-TAD | 0.43 |
| 3'SL-NAc-TAD | 0.39 |
| TAD | 1.00 |
| 3'SL-NAc-aniline | 0.08 |
| 3'SL-NAc-Ph-N=C=S | 0.66 |

B. Conjugation to Serum Albumin via APEA

APEA is coupled to carbohydrates and carbohydrate analogs by reductive amination, as described below for 3'-sialyllactose (3'SL). 5 mg of $NaBH_4$ and 2 mg of 3'sialyllactose are added to 0.25 ml APEA and incubated under stirring for 16 hr at 35° C. Excess reagent is destroyed by adding acetic acid to lower the pH to 5.6 in an ice bath. The sample is evaporated to dryness by rotary evaporation.

The sample is dissolved in 0.1 M pyridine/acetate buffer, pH 5.0 and chromatographed in the same buffer on BioGel P-2. The fractions that are both UV adsorbent and orcinol positive are combined and evaporated to dryness. The sample is dissolved in water and passed through a C18 column. The product (3'sialyllactose-APEA) is not retained by the column and is collected.

0.73 mg of 3'sialyllactose-APEA is added to 0.2 ml of 0.5 M NaAc and 0.4 ml ethanol. While stirring carefully, 1.6 μl of thiophosgene is added. Neutral pH is maintained by the addition of 0.2 M NaOH. After 10 min., the mixture is evaporated to near dryness and reconstituted with 0.8 ml of 0.1 M borate buffer, pH 9.5. Synthesis of the isothiocyanate derivative is monitored by TLC as described below.

0.2 mg of serum albumin is added directly to the 3'sialyllactose-APEA-isothiocyanate derivative. The reaction is incubated at room temperature under constant stirring for 48 hr and monitored by TLC. The 3'sialyllactose-albumin containing solution is then dialyzed against an appropriate buffer.

The TLC analyses are performed as described above, with the following Rf values:

| Compound | Rf Value |
|---|---|
| 3'SLac | 0.22 |
| 3'SLac-APEA | 0.057 |
| 3'SLac-APEA-isothiocyanate | 0.55 |
| 3'SLac-APEA-albumin | 0.00 |

C. Conjugation to Dendrimer Carrier Groups via APD

Carbohydrates and carbohydrate analogs may be coupled to generation 4 dendrimers via APD as described below for 3'sialyllactose. The carbohydrate portions of these conjugates may be obtained from commercial sources such as Oxford GlycoSystems, Rosedale, N.Y.

The APD linker arm is derived from p-trifluoroacetamidoaniline (TFAN), which is synthesized from 4-trifluoroacetamidonitrobenzene. 2.76 g of p-nitroaniline is dissolved in 25 ml of redistilled pyridine, and the dark yellow solution is cooled in an ice bath. 5 ml of trifluoroacetic anhydride is added dropwise to the solution under constant stirring. The solution is then filtered on a sintered glass filter and washed with cold water. The solid material is recrystallized by adding approximately 100 ml of ethanol and gradually adding an additional 50 ml of ethanol while heating to 60° C. under stirring. The solution is covered and placed in the refrigerator overnight for recrystallization.

The solution is refiltered on a sintered glass filter, and the crystals are washed with cold water and dried under high vacuum. Yield of 4-trifluoroacetamidonitrobenzene is about 90–92% and the melting point is 140° C. The crystals are stored under desiccation at −20° C. or immediately subjected to reductive hydrogenation.

Reductive hydrogenation is achieved by adding 2 grams of 4-trifluoroacetamidonitrobenzene to 50 mg of palladium on activated charcoal in 30 ml of ethanol. Hydrogen gas is bubbled in the solution at room temperature for 3 hr. The solution is then filtered on Whatman No. 1 paper to remove the charcoal. The filter is washed with ethanol and the filtrate is pooled with the washing and evaporated to dryness by rotary evaporation. The product is crystallized by dissolving the residue in 20–40 ml of ethyl ether. Hexane is gradually added and the light pink crystals are collected by filtration and washed with hexane. The resulting 4-trifluoroacetamidoaniline (TFAN) has a melting point of 118° C. and a yield of 76%.

TFAN is then used to couple the 3'sialyllactose to a dendrimer. In the first step of the reaction, the oligosaccharide is coupled to TFAN by reductive amination followed by acetylation. 2 mg of 3'sialyllactose is added to 10 mg of TFAN in 0.3 ml of ethanol/water 2:1 (v/v). 0.02 ml of glacial acetic acid and 6 mg of NaCNBH$_3$ is added under stirring. The glass vial is capped and incubated under stirring at 30° C. for 15–20 hr. The reaction is monitored by TLC, as described below.

0.05 ml of acetic anhydride is added and incubated at 30° C. for an additional 3 hr. The reaction is monitored for complete acetylation by TLC. The reaction is then transferred to a 13×100 mm glass test tube with a PTFE lined screw cap. 5 ml of ethyl acetate is added, followed by 5 ml of water for extraction. The phases are separated and the water phase is washed with another 5 ml of ethyl acetate. The water phases are combined and concentrated to 1–2 ml by rotary evaporation.

The concentrate is applied to a $C_{18}$ column (4×0.4 mm i.d.) preconditioned with methanol followed by water. After washing with 5 column volumes of water, the N-acetylated TFAN derivative of 3'sialyllactose is eluted with 5 column volumes of methanol. The sample is evaporated to dryness by rotary evaporation.

The second step of the reaction removes the trifluoro group from the nitrogen. The dry TFAN derivative is dissolved in 0.5 ml of 0.5 M NaOH and incubated at room temperature for 3 hr. The reaction is monitored by TLC.

The third step of the reaction converts the amine to an isothiocyanate. 1 ml of ethanol is added to the reaction, followed by 0.02 ml glacial acetic acid. The pH is adjusted to about 7 with 0.1 ml of 0.2 M NaOH. Under constant stirring, 0.004 ml of thiophosgene is carefully added. The pH is adjusted to above 5 with another 0.1 ml of 0.2 M NaOH. Conversion of the aromatic amine to the isothiocyanate is almost instantaneous.

The reaction product is extracted with 0.5 ml water and 1 ml ethyl ether. The upper phase (ether) is washed again with 0.5 ml water. The water phases are combined and rotary evaporated to 0.5–1 ml.

The last step of the reaction couples the isothiocyanate derivative to the dendrimer. The isothiocyanate derivative is transferred to a 5 ml vial containing an amount of a generation 4 dendrimer (Aldrich Chemical Co., Milwaukee, Wis.) in 0.1 M borate buffer at pH 9.4 sufficient to prepare a glycoconjugate with the desired mole ratio of carbohydrate to dendrimer. The pH of the solution is readjusted to 9.4 with 0.5 M NaOH. The reaction is incubated under constant stirring at room temperature for at least 20 hr, and is monitored by TLC. The reaction is then dialyzed against three changes of 20 mM NH$_4$HCO$_3$, lyophilized and the degree of coupling is characterized using standard assays for protein and sialic acid.

D. Conjugation to Dendrimer Carrier Groups via APEA

APEA is coupled to carbohydrates and carbohydrate analogs by reductive amination, as described below for 3'-sialyllactose (3'SL). 5 mg of NaBH$_4$ and 2 mg of 3'sialyllactose are added to 0.25 ml APEA and incubated under stirring for 16 hr at 35° C. Excess reagent is destroyed by adding acetic acid to lower the pH to 5.6 in an ice bath. The sample is evaporated to dryness by rotary evaporation.

The sample is dissolved in 0.1 M pyridine/acetate buffer, pH 5.0 and chromatographed in the same buffer on BioGel P-2. The fractions that are both UV adsorbent and orcinol positive are combined and evaporated to dryness. The sample is dissolved in water and passed through a C18 column. The product (3'sialyllactose-APEA) is not retained by the column and is collected.

0.73 mg of 3'sialyllactose-APEA is added to 0.2 ml of 0.5 M NaAc and 0.4 ml ethanol. While stirring carefully, 1.6 μl of thiophosgene is added. Neutral pH is maintained by the addition of 0.2 M NaOH. After 10 min., the mixture is evaporated to near dryness and reconstituted with 0.8 ml of 0.1 M borate buffer, pH 9.5. Synthesis of the isothiocyanate derivative is monitored by TLC as described below.

Generation 4 dendrimer is added directly to the 3'sialyllactose-APEA-isothiocyanate derivative in an amount sufficient to prepare a glycoconjugate with the desired mole ratio of carbohydrate to dendrimer. The reaction is incubated at room temperature under constant stirring for 48 hr and monitored by TLC. The 3'sialyllactose-dendrimer containing solution is then dialyzed against an appropriate buffer.

Example 2

Purification of EGF Receptor

This example illustrates the purification of EGF receptors from A431 cell membranes.

A. Preparation of Cell Membranes

Membranes were prepared by scraping A431 cells (American Type Culture Collection, Rockville, Md.) from 150 mm dishes of confluent cells in the presence of phosphate-buffered saline (PBS). The scraped cells were pelleted by centrifugation at 800 g and resuspended in 6 ml of 5 mM HEPES, pH 7.4, 5 mM $MgCl_2$, and 5 mM of β-mercaptoethanol. The cells were then homogenized with 30–50 strokes in a Dounce homogenizer using a tight-fitting pestle. 2.1 ml of 1 M sucrose was added to the homogenate and the homogenate was centrifuged at 1200 g for 10 minutes. The supernatant was then transferred to a polycarbonate tube and centrifuged at 100,000 g for 1 hr. The pellet was resuspended in 300 μl of 20 mM HEPES, pH 7.4, 100 mM NaCl, 5 MM $MgCl_2$. Protein concentration was determined as described in Peterson, *Anal. Biochem.* 83:346 (1977).

B. Purification of EGF Receptor from Cell Membranes

Carbohydrates such as 3' sialyllactose and carbohydrate analogs may be coupled to solid supports containing free amines, such as PharmaLink Gel (trademark of Pierce Chemical Co., Rockford, Ill.) or by way of aminophenylene diamine (APD) as described below for 3'-sialyllactose (3'SL). The carbohydrate portions of these conjugates may be obtained from commercial sources such as GlycoTech Corp., Gaithersburg, Md., or Oxford GlycoSystems, Rosedale, N.Y.

The APD linker arm is derived from p-trifluoroacetamidoaniline (TFAN), which is synthesized from 4-trifluoroacetamidonitrobenzene. 2.76 g of p-nitroaniline is dissolved in 25 ml of redistilled pyridine, and the dark yellow solution is cooled in an ice bath. 5 ml of trifluoroacetic anhydride is added dropwise to the solution under constant stirring. The solution is then filtered on a sintered glass filter and washed with cold water. The solid material is recrystallized by adding approximately 100 ml of ethanol and gradually adding an additional 50 ml of ethanol while heating to 60° C. under stirring. The solution is covered and placed in the refrigerator overnight for recrystallization.

The solution is refiltered on a sintered glass filter, and the crystals are washed with cold water and dried under high vacuum. Yield of 4 -trifluoroacetamidonitrobenezene is about 90–92% and the melting point is 140° C. The crystals are stored under desiccation at −20° C. or immediately subjected to reductive hydrogenation.

Reductive hydrogenation is achieved by adding 2 grams of 4-trifluoroacetamidonitrobenezene to 50 mg of palladium on activated charcoal in 30 ml of ethanol. Hydrogen gas is bubbled in the solution at room temperature for 3 hr. The solution is then filtered on Whatman No. 1 paper to remove the charcoal. The filter is washed with ethanol and the filtrate is pooled with the washing and evaporated to dryness by rotary evaporation. The product is crystallized by dissolving the residue in 20–40 ml of ethyl ether. Hexane is gradually added and the light pink crystals are collected by filtration and washed with hexane. The resulting 4-trifluoroacetamidoaniline (TFAN) has a melting point of 118° C. and a yield of 76%.

TFAN is used to couple oligosaccharides such as 3'sialyllactose to amine-containing proteins such as serum albumin. In the first step of the reaction, the oligosaccharide is coupled to TFAN by reductive amination followed by acetylation. 2 mg of 3'sialyllactose is added to 10 mg of TFAN in 0.3 ml of ethanol/water 2:1 (v/v). 0.02 ml of glacial acetic acid and 6 mg of $NaCNBH_3$ is added under stirring. The glass vial is capped and incubated under stirring at 30° C. for 15–20 hr. The reaction is monitored by TLC, as described below.

0.05 ml of acetic anhydride is added and incubated at 30° C. for an additional 3 hr. The reaction is monitored for complete acetylation by TLC. The reaction is then transferred to a 13×100 mm glass test tube with a PTFE lined screw cap. 5 ml of ethyl acetate is added, followed by 5 ml of water for extraction. The phases are separated and the water phase is washed with another 5 ml of ethyl acetate. The water phases are combined and concentrated to 1–2 ml by rotary evaporation.

The concentrate is applied to a $C_{18}$ column (4×0.4 mm i.d.) preconditioned with methanol followed by water. After washing with 5 column volumes of water, the N-acetylated TFAN derivative of 3'sialyllactose is eluted with 5 column volumes of methanol. The same is evaporated by dryness by rotary evaporation.

The second step of the reaction removes the trifluoro group from the nitrogen. The dry TFAN derivative is dissolved in 0.5 ml of 0.5 M NaOH and incubated at room temperature for 3 hr. The reaction is monitored by TLC.

The third step of the reaction converts the amine to an isothiocyanate. 1 ml of ethanol is added to the reaction, followed by 0.02 ml glacial acetic acid. The pH is adjusted to about 7 with 0.1 ml of 0.2 M NaOH. Under constant stirring, 0.004 ml of thiophosgene is carefully added. The pH is adjusted to above 5 with another 0.1 ml of 0.2 M NaOH. Conversion of the aromatic amine to the isothiocyanate is almost instantaneous.

The reaction product is extracted with 0.5 ml water and 1 ml ethyl ether. The upper phase (ether) is washed again with 0.5 ml water. The water phases are combined and rotary evaporated to 0.5–1 ml.

The last step of the reaction couples the isothiocyanate derivative to the amine containing solid support, such as PharmaLink Gel (Pierce Chemical Co., Rockford, Ill.). The isothiocyanate derivative is transferred to a 5 ml vial containing 25 mg PharmaLink gel in 0.1 M borate buffer at pH 9.4. The pH of the solution is readjusted to 9.4 with 0.5 M NaOH. The reaction is incubated under constant stirring at room temperature for at least 20 hr, and is monitored by TLC of the liquid phase. The solid support is then removed by filtration or centrifugation and washed three times with 20 mM $NH_4HCO_3$ and three times with PBS.

The resulting carbohydrate immobilized on a solid support is incubated with 0.5 to 1.0 mg of the proteins from an A431 cell lysate for 16 hr at 4° C. The solid support is then washed three times with PBS and twice with PBS containing 0.05% Triton X-100 and 10% glycerol. If the material is to be used directly in a kinase assay, it is washed one time with phosphorylation buffer. If the EGF receptor is to be eluted from the solid support, it is washed with a sufficient concentration of free 3' sialyllactose (e.g., 0.5 M) in PBS containing 0.05% Triton X-100 and 10% glycerol to elute the EGF receptor. The protein is then dialysed against PBS containing 0.05% Triton X-100 and 10% glycerol to remove the 3' sialyllactose.

Example 3

Competition Assay for Binding to EGF Receptor

This example illustrates a competition assay for the binding of a candidate compound to an EGF receptor.

A chimeric protein containing the extracellular portion of the EGF receptor fused to the constant portion of the heavy chain of γ immunoglobulin is prepared according to the method of Aruffo et al., Cell 61:1303–1313 (1990).

The chimeric protein (0.2 μg in 100 μl of PBS) is coated on a well of a Falcon Pro-Bind 96 well assay plate (Becton Dickinson, Lincoln Park, N.J.) by incubation at 4° C. overnight or by incubation at 37° C. for 2 hr. After this incubation, non-specific binding may be blocked by incubating the coated support with 3% bovine serum albumin in PBS for at least 1 hr at room temperature, followed by washing four times with PBS.

The immobilized chimeric protein is then incubated with 60 μl of 10 mM candidate compound (in PBS with 1% BSA) for 2 hr at room temperature. 60 μl of 1 μg/mL 3'-sialyllactose conjugated to a biotinylated BSA is then added to the mixture, and incubated with the immobilized chimeric protein for an additional 2 hr. The solid support is then washed with PBS, as before.

Bound 3'-sialyllactose is then detected using streptavidin, conjugated to horseradish peroxidase (Amersham, Arlington Heights, Ill.), according to the manufacturer's instructions. After incubation with streptavidin, the solid support is washed four times with PBS.

The presence of horseradish peroxidase is quantified by adding hydrogen peroxide and TMB, a substrate for HRP, stopping the reaction by the addition of 1 M $H_3PO_4$, and measuring the absorbance at 450 nm. Candidate compounds that generate a signal that is at least 50% of the signal achieved with 3'SL are considered to bind to EGF receptor.

Example 4

Direct Assay for Binding to EGF Receptor

This example illustrates a direct assay for identifying compounds that bind to the EGF receptor.

Compounds to be tested are allowed to bind to wells in a 96-well microtiter plate (e.g., Probind, Falcon, Lincoln Park, N.J.) or to PVDF membranes. The compounds are immobilized on the wells by incubation at 4° C. overnight or by incubation at 37° C. for 2 hr. After this incubation, non-specific binding is blocked by incubating the solid support with 3% bovine serum albumin in phosphate-buffered saline (PBS) for at least 1 hr at room temperature. The wells are then washed with PBS.

EGF receptors purified as in Example 2, are incubated with the coated wells for 2 hr at 37° C. in order to allow the EGF receptor to bind the immobilized compounds. The wells are then washed with PBS.

Bound EGF receptor is detected by incubating the wells with mouse anti-EGF receptor antibodies (Sigma, St. Louis, Mo. or UBI, Lake Placid, N.Y.). After washing the support, the support is incubated with horseradish peroxidase conjugated to goat anti-mouse secondary antibody (Amersham, Arlington Heights, Ill.). The support is then washed as above.

Horseradish peroxidase reporter groups are then quantified by incubating the support with substrate, as described in Example 3. Candidate compounds that generate a signal that is at least two-fold above background are considered to bind to EGF receptor.

Example 5

Inhibition of EGF Receptor Autophosphorylation

This Example illustrates the inhibition of immunoprecipitated EGF receptor autophosphorylation by carbohydrates of this invention.

EGF receptor was immunoprecipitated from detergent solubilized A431 cells with a polyclonal anti-EGF receptor antibody coupled to Protein A-agarose beads. The beads for immunoprecipitation are prepared by incubation of 2–5 μg of a polyclonal anti-EGF receptor antibody (UBI, Lake Placid, N.Y.) with 50 μl of Protein A-agarose beads (Sigma, St. Louis, Mo.) in a total volume of 300 μl PBS for 1 hr at room temperature. The armed beads are then incubated with 500 μg to 1.0 mg of the proteins from an A431 cell lysate for 16 hr at 4° C. The beads are then washed three times with PBS and once with phosphorylation buffer. The entire sample is used for one kinase reaction.

In the first experiment, equal portions of the immunoadsorbed EGF receptor complexes were incubated without carbohydrate, or with either 70 or 130 μg of 3'SL-HSA, in a total volume of 250 μl for 1 hr at room temperature. 100 ng of EGF was added to the samples, which were then incubated for 5 minutes in ice. 1 μCi of radiolabeled [$\gamma^{32}$P]ATP was added to each sample and, after 20 minutes of incubation on ice, the tubes were centrifuged for 20 seconds in a microfuge, the supernatant removed, and 20 μl of 2×electrophoresis buffer was added. Samples were boiled for 2 minutes and loaded on an 8% polyacrylamide gel. Following electrophoresis, the gel was dried and autoradiographed, and the radioactivity was quantified using a phosphoimage analyzer (BioRad, Hercules, Calif.).

The level of autophosphorylation, as measured by the amount of $^{32}$P incorporated into the immunoprecipitated EGF receptor, is shown in FIG. 1. These results indicate that 3'SL conjugated to HSA is an effective inhibitor of EGF receptor autophosphorylation.

In a second experiment, a series of carbohydrates according to this invention were evaluated for the ability to inhibit EGF receptor autophosphorylation. The assays were performed as described above, except that 5 μg of each carbohydrate was used. A dose titration curve (not shown) indicated that the 70 μg used in the first experiment was well above maximal inhibition, and that (for 3'SL-HSA) 5 μg was within the linear range of the inhibition curve.

Figure 2:
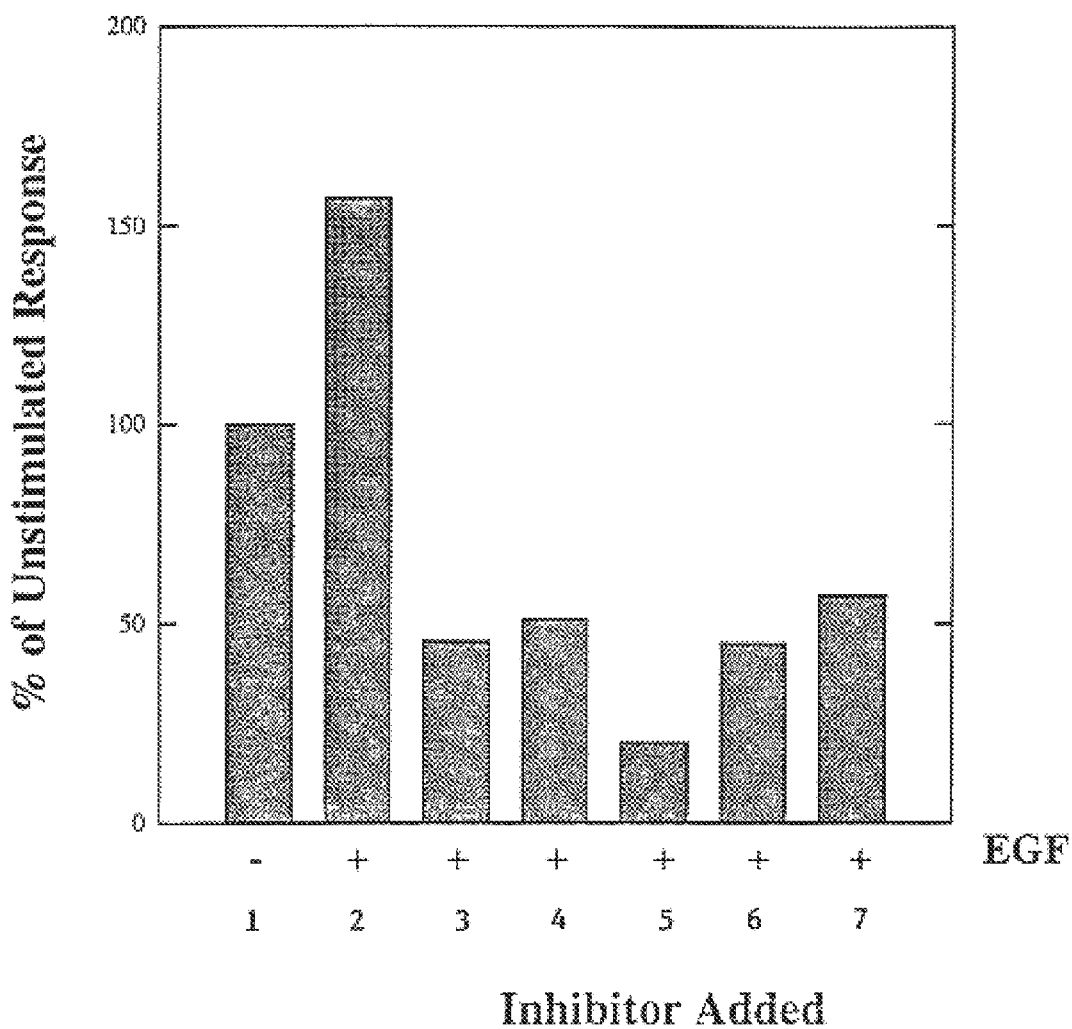
FIG. 2 shows the level of inhibition of EGF receptor autophosphorylation by a series of representative carbohydrates of this invention. Lane 1 shows the response in the absence of EGF, lane 2 shows the response in the presence of EGF without carbohydrate, and lanes 3–7 show the response in the presence of EGF and one of the following: LNnT-HSA, 3'SL-HSA, 6'SL-HSA, LSTa-HSA and 3'SL-HSA (repeat), respectively.

The level of autophosphorylation, expressed as percent of unstimulated response (i.e., $^{32}$P incorporation in the absence of EGF), is presented in FIG. 2, where lane 1 shows the response in the absence of EGF, lane 2 shows the response in the presence of EGF (without carbohydrate), and lanes 3–6 show the response in the presence of EGF and one of the following: LNnT-HSA, 3'SL-HSA, 6'SL-HSA and LSTa-HSA, respectively. Each of these conjugates was effective in inhibiting EGF receptor autophosphorylation. Lane 7 also shows the response in the presence of 3'SL-HSA, which demonstrates the reproducibility of this assay.

Figure 3:
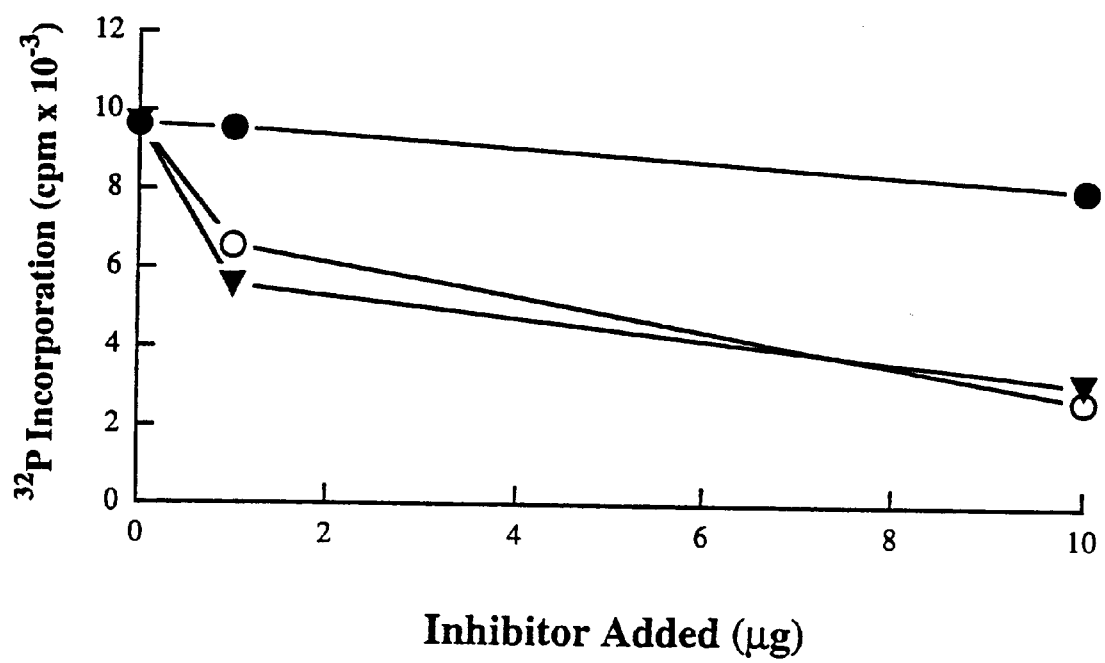
FIG. 3 illustrates the inhibition of EGF receptor autophosphorylation by 3' SL-BSA and 3' SL-dendrimer. (▼) 3'SL-BSA, (○) 3'SL-dendrimer, (●) BSA.

In a third experiment, 3'SL coupled to a dendrimer as described in Example 1 was evaluated for inhibition of EGF receptor autophosphorylation. The assay was performed as described above, using 1 or 10 μg of either 3'SL-BSA or 3'SL-dendrimer. The results, presented in FIG. 3, indicate that both 3'SL-BSA and 3'SL-dendrimer inhibit autophosphorylation.

Example 6

Inhibition of EGF Receptor Kinase Activity

This example illustrates the inhibition of EGF receptor kinase activity in cell membranes.

Cell membrane preparations containing EGF receptor were prepared as described in Example 2. Phosphorylation of membrane proteins by membrane kinases was carried out as described by Pike et al., *Proc. Natl. Acad. Sci USA* 79:1443 (1982), using 40 µg of A431 cell membrane preparations. Assays were carried out in a volume of 40 µl containing 20 mM HEPES, pH 7.4, 100 mM NaCl, 2 mM $MgCl_2$, and 100 µM sodium orthovanadate. Triton X-100 solubilized membrane (5 µg) was preincubated with or without carbohydrate (either 3'SL-BSA or 3'SL-dendrimer) for 30 minutes, and then with 50 ng EGF for 5 minutes prior to initiation of the reaction. The kinase reaction was started by the addition of 10 µM $[\gamma^{32}P]$ ATP (1,000–30,000 Ci/mmol) at 4° C., and was allowed to proceed for 5 minutes to allow for autophosphorylation. 2 mM RR-src peptide was then added. The reaction was allowed to proceed for an additional 10 minutes at 4° C., and was stopped by the addition of 50 µl ice cold 10% trichloroacetic acid. Following centrifugation, the supernatant containing the phosphorylated RR-src peptide was transferred onto phosphocellulose paper (Whatman P81, Whatman, Maidstone, England) and washed three times in 0.075 M phosphoric acid. The dried papers were then placed into a liquid scintillation counter.

Figure 4:
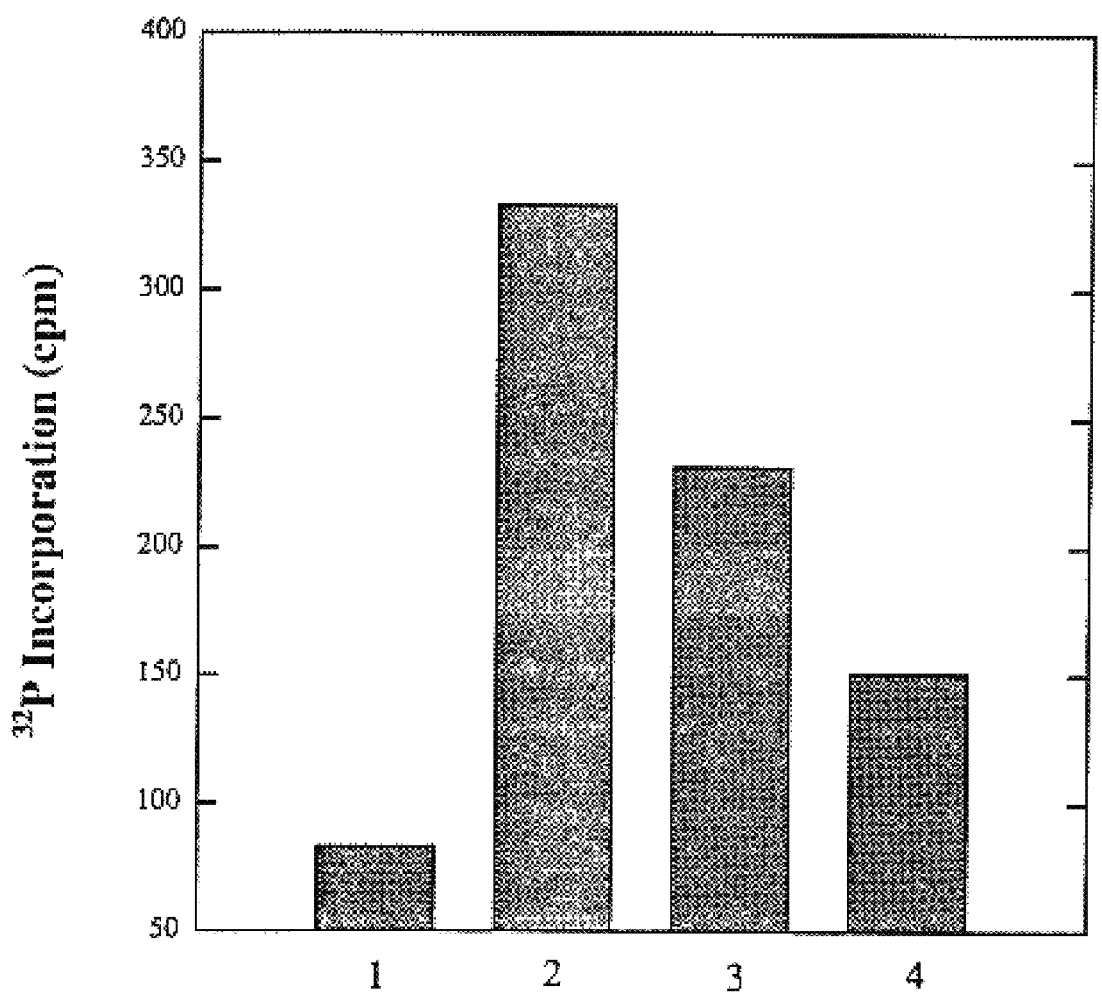
FIG. 4 shows the inhibition of EGF receptor kinase activity in cell membranes by 3' SL-BSA and 3' SL-dendrimer. $^{32}P$ incorporation is represented in the absence (Column 1) or presence (Column 2) of EGF without added carbohydrate. Columns 3 and 4 show inhibition of incorporation in the presence of EGF by 3'SL-BSA and 3'SL-dendrimer, respectively.

The results, shown in FIG. 4, are expressed as the mean of three replicates for each data point. Column 1 represents the incorporation of $^{32}P$ in the absence of EGF, and column 2 shows the incorporation in the presence of EGF, without carbohydrate. Columns 3 and 4 show the inhibition of incorporation (in the presence of EGF) by 3'SL-BSA and 3'SL-dendrimer, respectively.

These results show that both 3'SL-BSA and 3'SL-dendrimer inhibit EGF stimulated kinase activity.

Example 7

Measurement of EGF Receptor Kinase Activity in Intact Cells

Autophosphorylation of the EGF receptor in intact cells is determined with anti-phosphotyrosine antibody as described in Pike et al., *Proc. Natl. Acad. Sci. USA* 79:1443 (1982). Human epidermoid carcinoma cells (A1S) (cultured as described in Hanai et al., *J. Biol. Chem.* 263:10915 (1988)) are seeded in 25 $cm^2$ flasks in appropriate media with or without carbohydrate or carbohydrate analog. The cells are cultured for three days, and then transferred to serum-free media (2 ml) supplemented with 100 ng/flask of EGF for 10 minutes at 37° C. After washing twice with ice-cold PBS, the monolayer is solubilized with buffer containing 50 mM HEPES (pH 7.4), 150 mM NaCl, 100 mM NaF, 1 mM $MgCl_2$, 1.5 mM EGTA, 200 µM sodium orthovanadate, 1% Triton X-100, 10% glycerol, 1 mM PMSF, 10 µg/ml aprotinin, 5 mg/ml sodium deoxycholate, and 1 mg/ml sodium dodecylsulfate. After determination of the protein concentration of the lysates, 50 µg of soluble protein is resolved by SDS-PAGE and transferred electrophoretically onto nitrocellulose paper (BioRad, Hercules, Calif.). Phosphotyrosine containing proteins are identified with a mouse monoclonal anti-phosphotyrosine antibody PY-20 (ICN, Costa Mesa, Calif.) and detected by sequential blotting with biotinylated goat anti-mouse IgG, streptavidin alkaline phosphatase conjugate and BCIP/NBT (ICN).

Example 8

Incorporation of 3' Sialyllactose Analog into a Liposome

A liposome incorporating a carbohydrate is prepared by mixing carbohydrate (for example, 3'sialyllactose analog), dipalmitoyl phosphatidyl choline, and cholesterol (1:5:3 by weight) in methanol:chloroform (1:1) and drying the mixture. Phosphate buffered saline is added to the mixture and it is sonicated for 30 minutes to produce liposomes with a range of sizes. Liposomes with a narrow size distribution are isolated by filtration through a polycarbonate filter with an 80 to 100 nm pore size, yielding liposomes with similar diameters.

To incorporate a toxic compound into the liposome, an agent such as daunomycin is included into the mixture as follows:

A liposome is prepared by mixing carbohydrate, dipalmitoyl phosphatidylcholine, cholesterol, and an antioxidant such as Vitamin E (7.5:38:23:1 by weight) in methanol:chloroform (1:1) and drying the mixture. 150 mM ammonium sulfate, pH 5.5, is added to the mixture and it is sonicated for 30 minutes to produce liposomes with a range of sizes. Liposomes with a narrow size distribution are isolated by passing this mixture through a polycarbonate filter with 80 to 100 nm pore size twenty to thirty times, to yield liposomes with a similar diameter. The liposomes are then dialyzed with 5% glucose, pH 7, to set up a pH gradient. The daunomycin is incorporated into the liposomes by heating the liposomes at 60° C. for one hr with 3.8 M daunomycin in 5% glucose, pH 7. The preparation is cooled to room temperature and unincorporated daunomycin is removed by ion exchange.

Example 9

Assay for Binding of EGF Receptor to Immobilized 3'SL-HSA

3'SL-HSA is incubated in Falcon probind™ microtiter plate (Plate 1) at serial dilutions in Tris-$CA^{++}$ buffer (0.05M Tris HCl, 0.15M NaCl, 2 mM $CaCl_2$, pH 7.4). Plate 1 is covered and incubated overnight at 4° C. After incubation, 100 µl/well of 2% BSA in Tris-$Ca^{++}$ buffer is added and incubated at room temperature for 2 hours. This is a minimum time and can be extended if necessary. During incubation, EGF receptor (Sigma cat#E-1886) is titrated (2×serial dilution) in 1% BSA in Tris-$Ca^{++}$ buffer using U-shaped low bind microtiter plates (Plate 2). Serially dilute up to row 9. Rows 10, 11, and 12 should be just buffer. Final volume should be 120 µl/well and the first well should contain 10 µg/ml of EGF receptor. Plate 1 is washed four times with Tris-$Ca^{++}$ buffer in the automatic plate washer. 100 µl/well is transferred from Plate 2 to Plate 1 starting from lowest concentration of EGF receptor using an 8-channel pipettor from right to left. Discard Plate 2. Plate 1 is incubated while rocking at room temperature for 2 hours; and washed four times with Tris-$Ca^{++}$ buffer using automatic plate washer.

100 µl/well of 1/1,000 dilution of anti-EGF receptor antibody (Sigma cat#E-2760) in Tris-$Ca^{++}$ buffer, 1% BSA is added. Incubate while rocking at room temperature for 1 hour. Wash four times with Tris-$Ca^{++}$ buffer using automatic plate washer. 100 µl/well of peroxidase-labeled goat anti-mouse IgG (KPL labs, cat#074-1806) at 1 µg/ml in Tris-$Ca^{++}$ buffer, 1% BSA is added. Incubate while rocking at room temperature for 1 hour. Wash four times with Tris-$Ca^{++}$ buffer using automatic plate washer.

Figure 5:
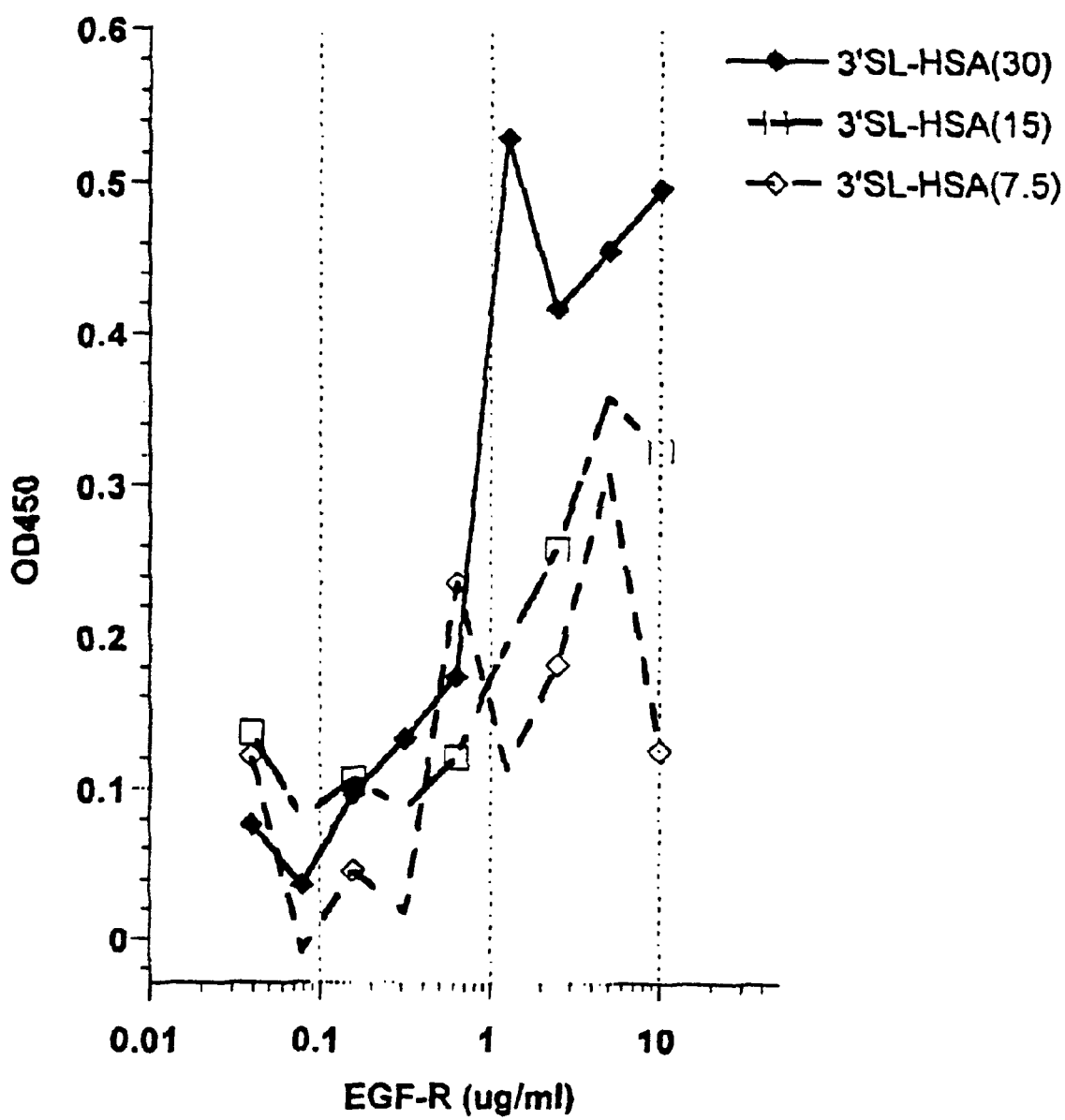
FIG. 5 illustrates the binding of EGF receptor (EGF-R) to immobilized 3'SL-HSA.

100 μl/well of Substrate (mix TMB reagent and $H_2O_2$ at 1:1 ratio) is added with an 8-channel pipettor from right to left. Incubate at room temperature for 3 minutes. The reaction is stopped by adding 100 μl/well of 1M $H_3PO_4$ using the 8-channel pipettor from right to left. Read absorbance of light at 450 nm. The results are shown in FIG. 5.

Example 10

Binding of EGF Receptor External Domain to Immobilized Neoglycoconjugates

Figure 6:
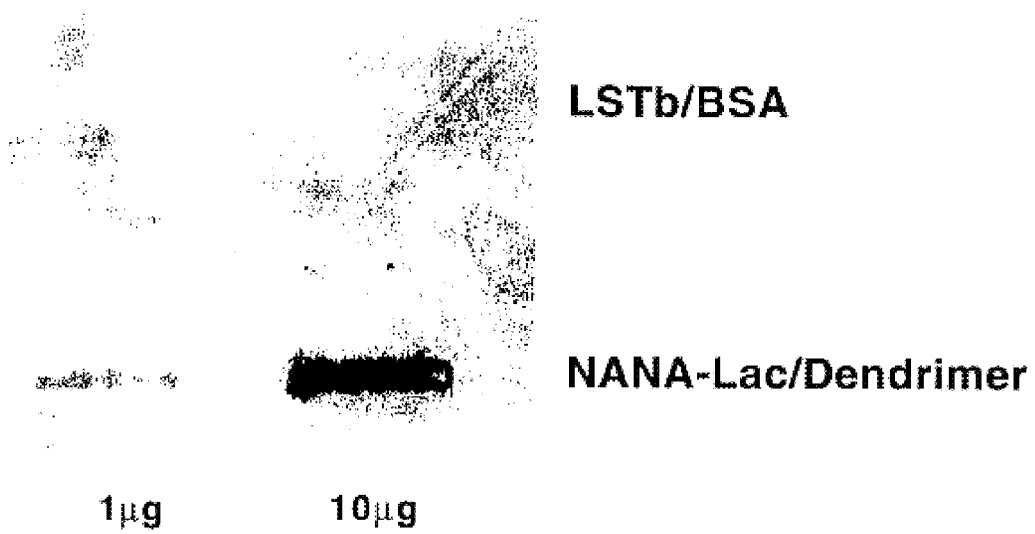
FIG. 6 shows the binding of the external domain of EGF receptor to immobilized neoglycoconjugates.

Neoglycoconjugates (LSTb/BSA or 3'SL/dendrimer) were spotted at the amounts indicated on a PVDF membrane (Millipore). The non-specific binding sites were then blocked with 3% BSA in phosphate-buffered saline (PBS) for 30 min. at room temperature. The PVDF membrane was then incubated for two hours with A431 cell (human epidermoid carcinoma) culture supernatant enriched in EGF receptor external domain. After washing with PBS, the membrane was then incubated with anti-EGF receptor monoclonal antibody (UBI), directed against the external domain, at a 1/1000 dilution for 1 hour at room temperature. The immunocomplex was then detected using a secondary antibody linked to horseradish peroxidase and an ECL kit (Amersham). The results are shown in FIG. 6.

The external domain of the EGF receptor was isolated from the cell culture supernatants of A431 cells. This soluble form of the receptor containing the EGF binding domain arises from alternate splicing of the full length message. The material used in the above assay was prepared by ultra filtration of A431 cell culture supernatant to concentrate EGF binding proteins. This was followed by immunoadsorbtion with anti-EGF receptor antibodies directed against the cytoplasmic domain of the receptor in order to remove any full length receptor in culture supernatant. The presence of the external domain was confirmed by western blot.

Example 1

Effect of 3'SL Conjugates on the Proliferation of Human Epidermoid Carcinoma Cells (A1S)

Figure 7:
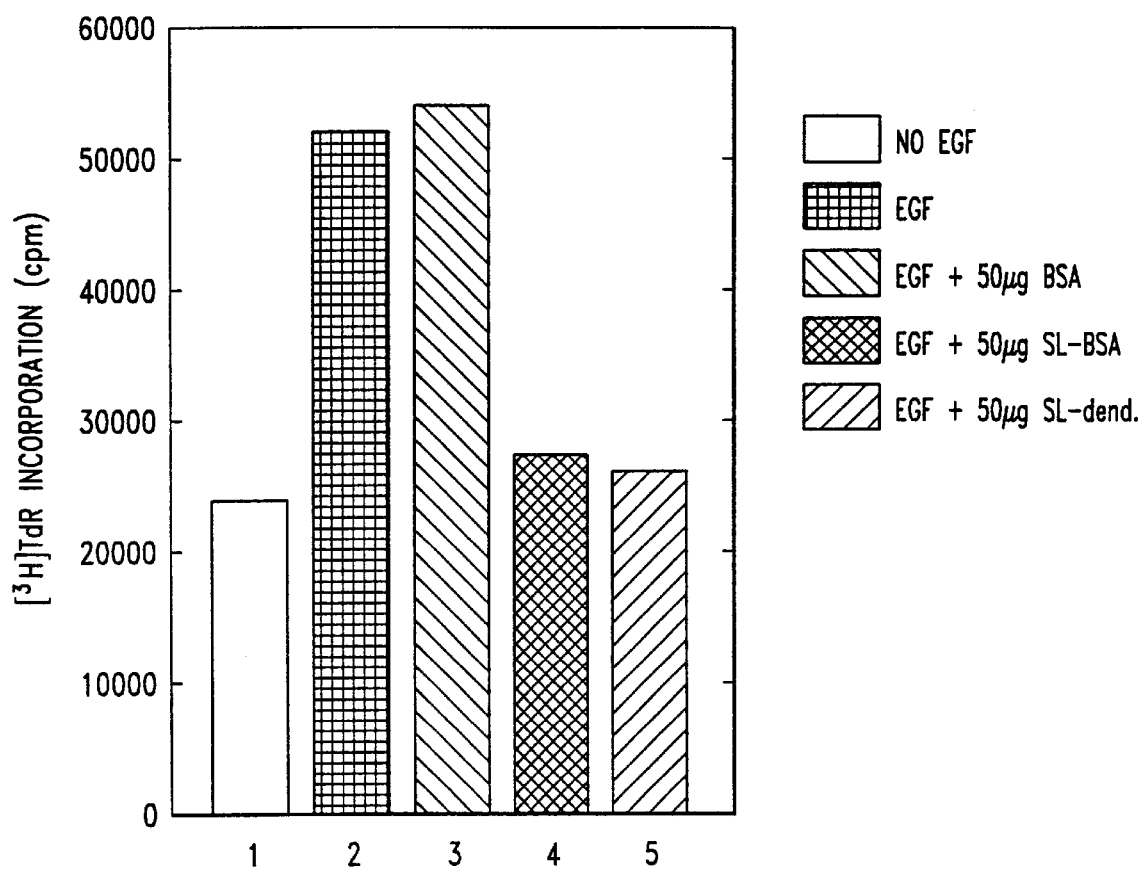
FIG. 7 illustrates the effect of 3'SL conjugates on the proliferation of human epidermoid carcinoma cells (A1S).

The effects of 3'SL/BSA and 3'SL/dendrimer were tested for their ability to inhibit tumor cell growth in culture. For these experiments, 1×10⁴ A1S cells were seeded in triplicate onto 24-well plates (Falcon) in DMEM-F12 containing 10% supplemented calf serum. After cell attachment to the plastic substratum (4–5 hours), the medium was removed and replaced with DMEM-F12 containing 1% FBS. The 3'SL conjugates were added at the amount indicated in FIG. 7 per ml when the medium was replaced. The cells were then allowed to grow in culture for 48 hours. The cells were stimulated with 100 ng/ml EGF for 6 hours prior to addition of [³H]TdR for 18 hours. The data presented in FIG. 7 are reported as the average DPM incorporated per triplicate samples. The data presented in the figure show that the 3'SL conjugates are able to inhibit the EGF dependent cell growth of A1S tumor cells.

All publications and patent applications mentioned in this specification are herein incorporated by reference to the same extent as if each individual publication or patent application was specifically and individually incorporated by reference.

From the foregoing, it will be appreciated that, although specific embodiments of the invention have been described herein for the purpose of illustration, various modifications may be made without deviating from the spirit and scope of the invention.

What is claimed is:

1. A pharmaceutical composition, comprising:

(a) a compound having the formula:

wherein X is a sialic acid or a non-saccharide group that mimics the structure of a sialic acid group Y and Z are independently a monosaccharide residue or a non-saccharide group that mimics the structure of a monosaccharide residue, and R is a carrier group, or a carbohydrate compound having a type 2 saccharide chain without a sialic acid residue or an analog thereof, and with a carrier group, wherein the carrier group is a cytotoxic agent, toxin or radionuclide that inhibits tumor cell growth or kills tumor cells; and (b) a pharmaceutically acceptable carrier or diluent.

2. The composition of claim 1 wherein said compound is incorporated into a liposome.

3. The composition of claim 1 wherein the compound is 3'-sialyllactose or an analog thereof.

4. The composition of claim 3 wherein the compound is 3'-sialyllactose.

5. The composition of claim 3 or 4 wherein said compound is incorporated into a liposome.

* * * * *